United States Patent [19]

Schneider

[11] Patent Number: 5,140,902

[45] Date of Patent: Aug. 25, 1992

[54] INK TRANSFER ROLLER

[75] Inventor: Georg Schneider, Würzburg, Fed. Rep. of Germany

[73] Assignee: Koenig & Bauer AG, Wurzburg, Fed. Rep. of Germany

[21] Appl. No.: 719,004

[22] Filed: Jun. 21, 1991

[30] Foreign Application Priority Data

Jul. 4, 1990 [DE] Fed. Rep. of Germany ....... 4021183

[51] Int. Cl.$^5$ .............................................. B41F 13/08
[52] U.S. Cl. .................................... 101/376; 101/251; 73/150 R
[58] Field of Search ............... 101/251, 492, DIG. 45, 101/375, 376; 73/150 R, 150 A; 427/8

[56] References Cited

U.S. PATENT DOCUMENTS

| 2,825,225 | 3/1958 | Connell et al. | 73/150 R |
| 3,537,394 | 11/1970 | Swapp | 101/376 |
| 3,675,476 | 7/1972 | Zapfe | 73/150 R |

OTHER PUBLICATIONS

Technological Institute of Darmstadt-Dr.-Ing. Michael Gluck and Jorge Rodriguez-Giles-Published: Jan. 1979.
Fogra-Forschungsbericht-Title: Prufmoglichkeiten mit Probedruckgeraten Author: Karl-Adolf Falter-Published: 1976.

Primary Examiner—Edgar S. Burr
Assistant Examiner—Lynn D. Hendrickson
Attorney, Agent, or Firm—Jones, Tullar & Cooper

[57] ABSTRACT

An ink transfer roller assembly which is usable to evaluate the smearing behavior of ink on a print carrier utilizes a central disk having a resilient oleophilic periphery and two side disks of smaller radii. The oleophilic surface is pressed against a freshly printed surface and is rolled off the printed area. Ink retained by the resilient roller is transferred to the previously uninked surface and is evaluated for ink smearing.

3 Claims, 1 Drawing Sheet

5,140,902

INK TRANSFER ROLLER

FIELD OF THE INVENTOR

The present invention is directed generally to an ink transfer roller. More particularly, the present invention is directed to an ink transfer roller for use in determining the smearing behavior of ink. Most specifically, the present invention is directed to an ink transfer roller and to a method for using the ink transfer roller to determine the smearing characteristics of ink printed on paper, particularly by a newspaper rotary press. The ink transfer roller is used to contact a freshly printed image that has been allowed to dry for a selected period of time. The roller has an oleophilic portion that removes any wet ink from the printed image. This removed ink is then transferred to a non-printed area of the printed product and the resulting printed image can be analyzed to provide an indication of the ink smear characteristics of the ink.

DESCRIPTION OF THE PRIOR ART

The smearing behavior of freshly printed ink on paper is an important characteristic of the ink itself and of the paper on which it is printed. In an institute report by the Technological Institute of Darmstadt, which was published in January 1979, the measuring of the dryness degree of a printed ink film on a running paper web was discussed. In this report, and in prior procedures, the freshly printed ink is smeared by means of a smearing strip. The resulting smearing trace is then inspected. In this inspection procedure, the diminution of the luminance of the smearing trace, in comparison to the luminance of a non-printed surface is used as the evaluation criterion to ascertain the amount of ink smearing.

The production of an ink smearing trace requires the use of quite costly test equipment. The ink smearing can only be effected on the product on which the specimen print has already been made. In addition, the smearing trace must also be inspected over the entire area of the smear. This prior art ink smearing determination procedure cannot readily be accomplished without the necessary expensive equipment and is sufficiently difficult to do that a press operator may well not be able to do a satisfactory test procedure.

It will thus be apparent that a procedure and apparatus is required by which the ink smearing characteristics of a printing ink on a paper web can be readily and easily ascertained. The ink transfer roller and its method of usage, as will be discussed in detail subsequently, provides such an apparatus and procedure and is a substantial improvement over the prior art.

SUMMARY OF THE INVENTION

It is an object of the present invention to provide an ink transfer roller.

Another object of the invention is to provide a method for evaluating the smearing behavior of ink printed on paper.

A further object of the present invention is to provide an ink transfer roller having an oleophilic, resilient central roller.

Yet another object of the present invention is to provide an ink transfer roller that is manually operable.

Still a further object of the present invention is to provide an ink transfer roller having an oleophilic central roller and two oleophobic outer rollers.

Even yet another object of the invention is to provide an ink transfer roller that is inexpensive and easily operable.

As will be discussed in detail in the description of the preferred embodiment which is set forth subsequently, the ink transfer roller is usable to ascertain the smearing behavior of ink which has been printed on paper. The ink transfer roller assembly is hand operable and utilizes a central roller that has a resilient, oleophilic periphery. This central roller is bounded by two less resilient oleophobic rollers whose radii are less than the radius of the central roller. A sample of the freshly printed paper is allowed to dry for a specified period of time. The oleophilic roller is then run across the surface at a pressure determined by the engagement of the oleophobic rollers with the surface. The ink picked up by the oleophilic surface is applied to a non-printed surface of the paper and can be evaluated.

The method of determining ink smearing characteristics in accordance with the present invention can be utilized at any time and place. It does not require sophisticated test equipment or a highly trained operator. The ink transfer roller itself is readily portable and is inexpensive. It is very easy to operate so that virtually every press operator can carry his own ink transfer roller with him.

The ink surface or ink line picked up by the oleophilic surface of the ink transfer roller assembly can be transferred with a defined force that is dependent on the difference in radii between the oleophilic and oleophobic rollers. Only the transferred ink surface or the transferred ink line has to be inspected.

The ink transfer roller and its method of usage in accordance with the present invention is simple to use and is economical. It allows the ink smearing behavior of the ink printed on the paper to be evaluated in a simple, expeditious manner. The apparatus and procedure of the present invention is a substantial advance in the art.

BRIEF DESCRIPTION OF THE DRAWINGS

While the novel features of the ink transfer roller assembly and the method of usage for the evaluation of the smearing behavior of ink in accordance with the present invention are set forth with particularly in the appended claims, a full and complete understanding of the invention may be had by referring to the detailed description of the preferred embodiment which is presented subsequently, and as illustrated in the accompanying drawings, in which:

DESCRIPTION OF THE PREFERRED EMBODIMENT

Figure 1:
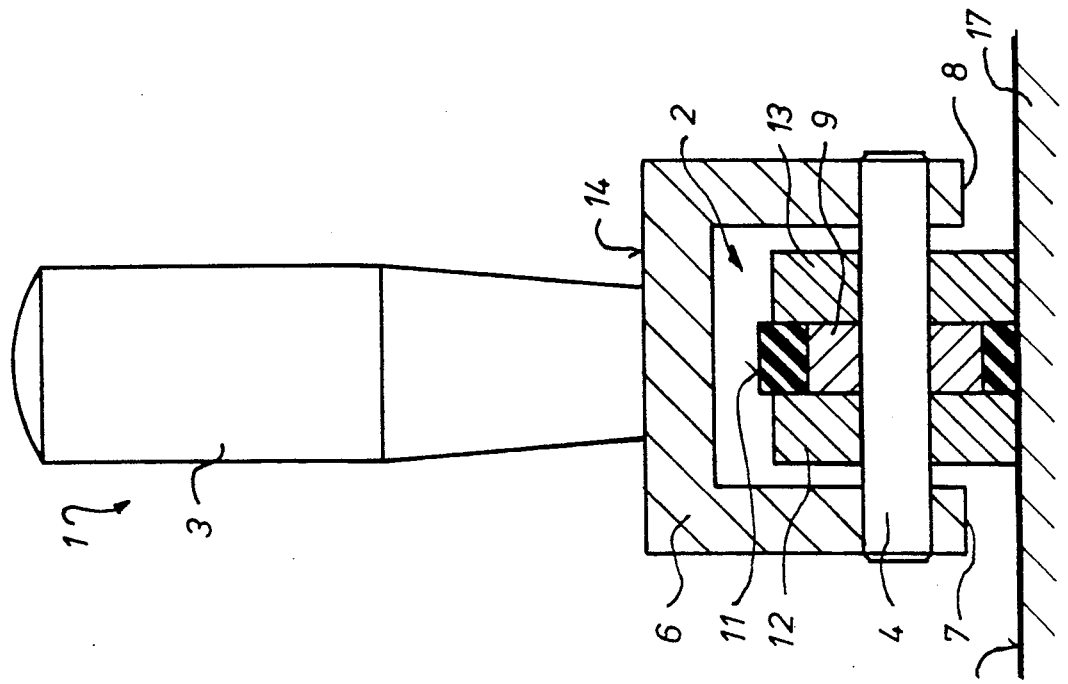
FIG. 1 is a front elevation view of the ink transfer roller assembly of the present invention.

Referring initially to FIG. 1, the ink transfer roller assembly, generally at 1, in accordance with the present invention includes a rotatably supported reel assembly 2 that is supported by a generally U-shaped support 6. A handle 3 is attached to the U-shaped support 6 and is graspable by the operator to manipulate the reel assembly 2.

The reel assembly 2 is fixedly secured to a transverse shaft 4. This shaft 4 is, in turn, rotatably supported in bores in side legs of the U-shaped support 6, as may be seen in FIGS. 1 and 2. The ends of shaft 4 pass through the side arms of the U-shaped support generally near free lower ends 7 and 8 of support 6, as seem in FIG. 2. The reel assembly 2 is sized so that it extends below the lower ends 7 and 8 of the side arms of the U-shaped support 6.

A central disk-shaped ink transfer roll 9 is provided with an oleophilic, easily deformable resilient periphery 11. A pair of less resilient or less deformable side disks 12 and 13 sandwich the central disc 9. These side disks 12 and 13 are, in comparison with the resilient outer periphery 11 of the central disk 9, rigid and ink-repellent.

A radius of the side disks 12 and 13 is smaller than a radius of the central disk 9. In the preferred embodiment, the central disk may have a radius of 18 mm. The radii of the two side disks 12 and 13 may each be 17 mm.

The handle 3 of the ink transfer roller 1 is secured by any suitable means to the upper cross member 14 of U-shaped support 6. The ink transfer roller assembly 1 is thus easily grasped and manipulated. The shape of handle 3 is exemplary and could be shaped as desired.

Figure 2:
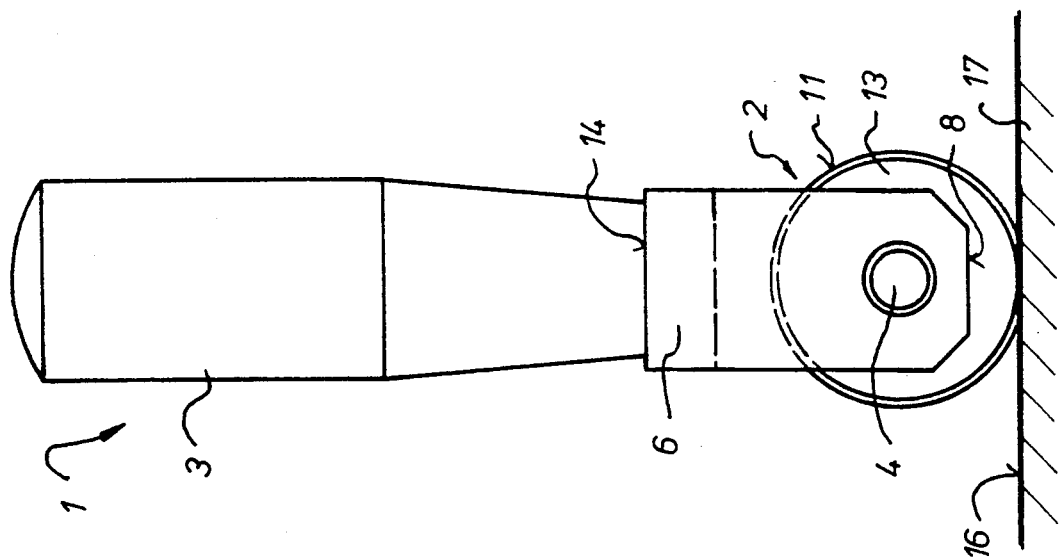
FIG. 2 is a side elevation view of the ink transfer roller assembly.

In accordance with the method of evaluating the smearing behavior of ink, a freshly printed paper web 16 is positioned on a firm base surface 17, such as a measuring table, as may be seen in FIGS. 1 and 2. The printed portion of the printed paper web 16 is reviewed and a relevant printed portion or printed line is selected. Preferably, this printed portion or line is a full tone portion or line. After the passage of a previously determined period of time, such as, for example, 20 seconds, this chosen line or area of print on printed paper web 16 is overrun by the reel assembly 2 of the ink transfer roller assembly 1. The oleophilic periphery 11 of the central disk 9 is caused to engage the ink whose smearing behavior is to be evaluated. Sufficient pressure is applied to the reel 2 through the handle 1 that the resilient periphery 11 is compressed to the extent that it forms a bearing surface with the peripheral portion of the side disks 12 and 13.

Ink in the area being evaluated is picked up by the oleophilic surface 11 of the central disk 9 to a degree determined by its wetness and its propensity to smear. This ink that adheres to resilient periphery 11 of the central disk 9 is then transferred, by continuation of the rolling movement of the reel 2, to a non-printed area of the paper web or similar print carrier 16. This ink is thus now transferred to the previously non-printed area of the paper web 16. This print that has been made by the oleophilic, resilient periphery 11 of the central disk 9 of the reel assembly 2 can then be inspected and evaluated either visually or by use of suitable equipment, such as a densitometer. The ink density on the print carrier, as applied thereto by the ink transfer roller assembly of the present invention, will provide the printer with usable information about the smearing tendency of the ink being used and its interaction with the printing paper being used.

While a preferred embodiment of an ink transfer roller assembly and its method of usage in the evaluation of the smearing behavior of ink in accordance with the present invention has been fully and completely set forth hereinabove, it will be apparent to one of skill in the art that a number of changes in, for example, the overall sizes of the central and side disks, the shape of the handle, the types of printing inks and print carriers and the like may be made without departing from the true spirit and scope of the invention, which is accordingly to be limited only by the following claims:

What is claimed is:

1. A method for evaluating the smearing behavior of ink comprising:
   printing an ink to be evaluated onto a print carrier;
   allowing said printed ink on said print carrier to dry for a selected time;
   contacting a printed area on said print carrier with an ink transfer means;
   removing a portion of said printed ink from said printed area on said ink transfer means;
   printing a previously unprinted area of said print carrier with said removed printed ink on said ink transfer means;
   evaluating said printing of said previously unprinted area; and
   ascertaining the smearing behavior of said ink.

2. An ink transfer roller assembly usable to remove freshly printed ink from a printed surface and to transfer the removed ink to an unprinted surface, said ink transfer roller assembly comprising:
   an ink transfer roll having an easily deformed, smooth cylindrical resilient oleophilic periphery printing type which is engagable with a freshly printed ink surface to remove ink from the freshly printed ink surface, said ink transfer roll and said oleophilic periphery forming a central disk having a first radius;
   first and second side disks positioned on first and second sides of said central disk, said first and second side disks having oleophobic, rigid surfaces, said first and second side disks having second radii, said first radius being greater than said second radii, said resilient periphery of said central disk extending radially outwardly beyond said first and second side disks except where said resilient periphery is deformed inwardly and has the same radius as said first and second side disks by engagement with a printed surface from which ink is to be removed;
   means for supporting said ink transfer roll and said oleophilic periphery together with said first and second side disks on a rotatable shaft for rotation as a unit to form an ink transfer reel; and
   means for facilitating manual manipulation of said ink transfer reel.

3. The ink transfer roller assembly of claim 2 wherein said means for supporting said ink transfer reel for rotation as a unit includes rotatably supporting said rotatable shaft on spaced legs of a generally U-shaped support and further wherein said means for manual manipulation of said ink transfer reel includes a handle secured to a cross member of said generally U-shaped support.

* * * * *